United States Patent [19]

Sharpe

[11] Patent Number: 4,621,619

[45] Date of Patent: Nov. 11, 1986

[54] RETRACTOR HAVING MEANS FOR ATTACHMENT TO PATIENT'S SKIN

[75] Inventor: David T. Sharpe, Leeds, England

[73] Assignee: Plastech Research & Design Limited, Leeds, England

[21] Appl. No.: 709,325

[22] Filed: Mar. 7, 1985

[30] Foreign Application Priority Data

Mar. 10, 1984 [GB] United Kingdom ............... 8406333

[51] Int. Cl.⁴ .............................................. A61B 17/02
[52] U.S. Cl. ............................ 128/20; 128/DIG. 15
[58] Field of Search ......................... 128/20, DIG. 15

[56] References Cited

U.S. PATENT DOCUMENTS

| | | | |
|---|---|---|---|
| 1,601,035 | 9/1926 | Nauth | 128/20 |
| 2,564,118 | 8/1951 | Mahorner | 128/20 |
| 2,642,862 | 6/1953 | Jackson | 128/20 |
| 2,701,562 | 2/1955 | Michael et al. | 128/20 |
| 2,717,592 | 9/1955 | Swineheart | 128/17 |
| 3,490,455 | 1/1970 | Illig | 128/20 X |
| 3,522,800 | 8/1970 | Lesser | 128/20 |
| 4,037,589 | 7/1977 | McReynolds | 128/20 |
| 4,051,844 | 10/1977 | Chiulli | 128/20 |
| 4,074,397 | 2/1978 | Rosin | 128/DIG. 15 |
| 4,412,532 | 11/1983 | Anthony | 128/20 |
| 4,432,347 | 2/1984 | Clavin | 128/20 |

FOREIGN PATENT DOCUMENTS 270961 8/1983 Spain .

Primary Examiner—William H. Grieb
Attorney, Agent, or Firm—Fred Philpitt

[57] ABSTRACT

The invention defines a plastics disposable, hand applied medical retractor for retracting flesh at the edges of an incision or aperture in the human or animal body. At one end the retractor has a sharply inturned hook portion on the end of which are short, sharp, triangular teeth for impaling the flesh. The retractor bows upwardly from the hook portion and back down to a pad which has an adhesive undersurface so that it can be pressed directly to the skin so as to anchor thereto to keep the pulled back flesh in the retracted position. The said bowing allows the pulled back flesh to bunch upwardly to prevent such flesh from forcing the teeth out of engagement with the flesh and also provides inherent springiness tension in the retractor when it is applied improving its performance. Instead of the pad having adhesive it may have one part touch and close fastener, the other part being previously applied to the skin by pressure sensitive adhesive.

12 Claims, 11 Drawing Figures

U.S. Patent  Nov. 11, 1986  Sheet 1 of 3  4,621,619
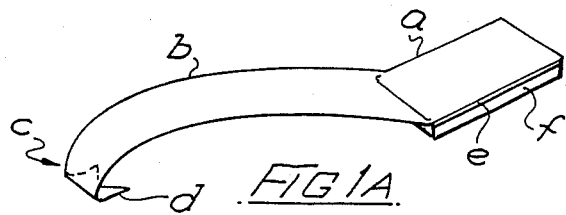
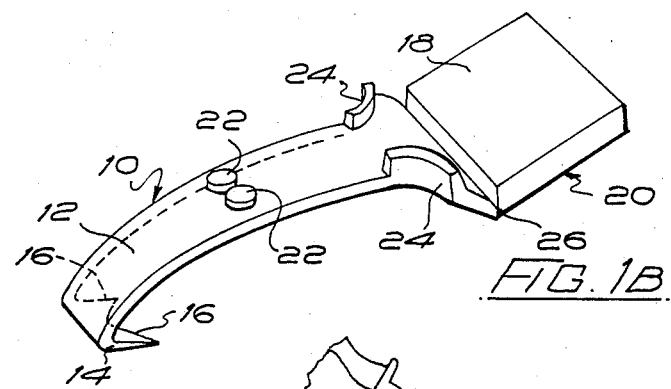
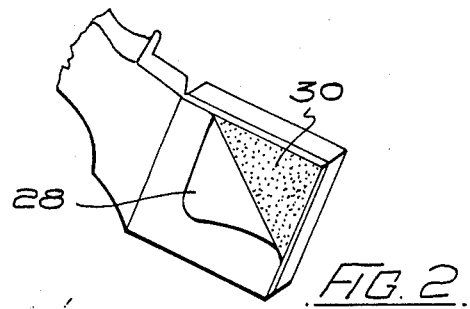
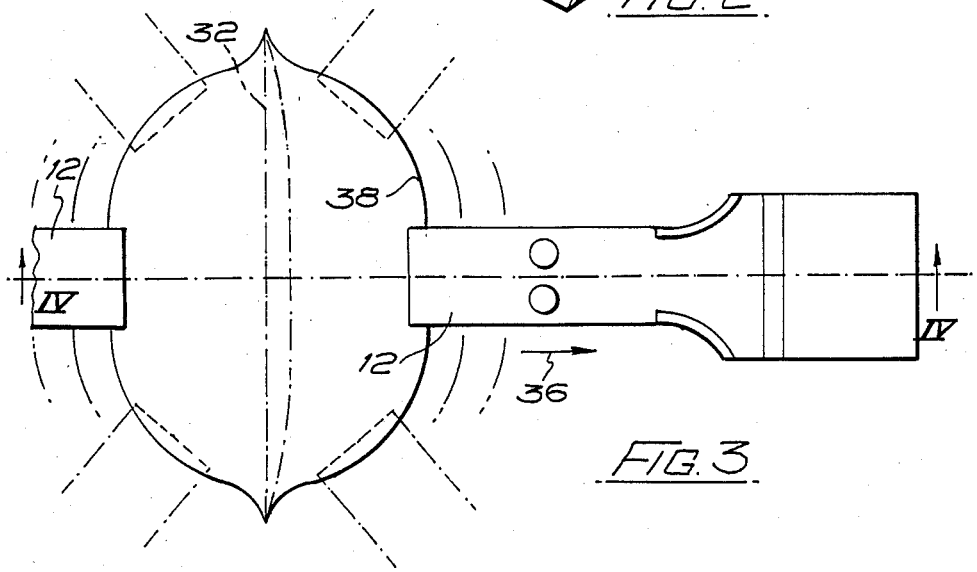

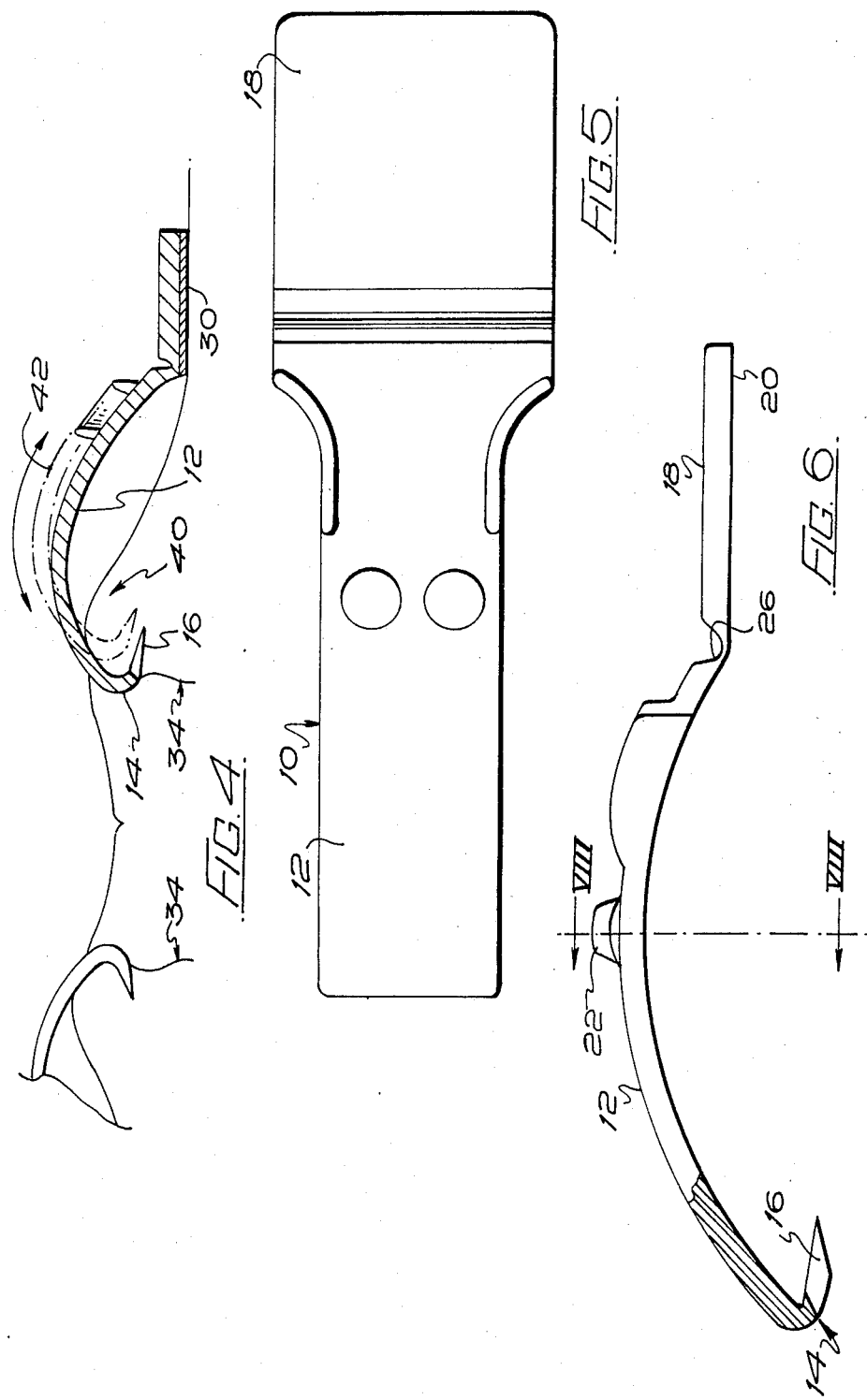

RETRACTOR HAVING MEANS FOR ATTACHMENT TO PATIENT'S SKIN

This invention relates to medical retractors, and in particular concerns a retractor for holding back of the tissue of an animal or human at an aperture thereof or following the making of an incision therein.

When an incision is made in human skin, normally, because of the resilience of the tissue and skin, the incision will tend to remain closed, and for a surgeon to perform an operation through the incision it is necessary that the tissue at the edges of the incision be held back to give the surgeon access. Retractors are used for this purpose, and most usually, the retractors are held by assistants and comprise metal instruments having handle portions and hooked ends which can engage the incision edges. In another construction, by virtue of the design of the retractor, spaced separating members which engage the incision edges are held in spaced condition by spring or jack means or the like. The latter type of equipment is relatively complicated mechanically, but it does remove the need for the same number of assistants as may be required when using hand held retractors.

There has been proposed a retractor comprising a straight elongated member having a hooked end adapted specifically for catching under the eyelid to retract same to expose the eye more for performing operations on same. It is suggested that a strip of sticking plaster may be used for holding this retractor in position. It is suggested that the sticking plaster may be applied over the end of the retractor remote from hooked end so that the ends of the sticking plaster adhere to the skin whilst the centre portion overlies and adheres to the said retractor end. This retractor and its application have a number of disadvantages. Firstly, as the sticking plaster is flexible it will tend to yield under the tensile forces which exist within the retractor when it holds back the tissue making the retractor less effective. Also, as the sticking plaster must ride over the end of the retractor, which has a finite thickness there will be a tendency for the plaster to peel away from the skin, and retractor could be lost.

Also, the application of sticking plaster over the retractor requires the use of two hands and is difficult as the retractor must be held in the retracted position, in which it is under the tension created by the tendency of the tissue to return to its natural position.

Furthermore, the sticking plaster in being applied to the skin at opposite sides of the retractor end takes up valuable working space in the aperture or incision area.

The present invention seeks to provide a simply applied retractor device enabling the holding back of tissue in the region of an incision or aperture in human or animal tissue without requiring the use of an assistant to hold the retractor whilst the surgeon or other medical practitioner works through said incision or aperture.

The invention provides therefore in a first aspect a rectractor for hand application and comprising at one end hook means for hooking onto the edge of an aperture or incision in tissue whereby with the hook means engaging the tissue, the edge of the aperture or incision can be pulled back by pullilng the retractor to improve access through said aperture or incision, and the retractor at a location spaced from said hook means can be anchored to keep the tissue in the held back position, and wherein at said location the retractor has a portion having an adhering surface clipping, locking means which can be adhered to clipped or locked to the skin or a means applied previously to or over the skin whereby the retractor can be used by hooking the hook means onto said edge followed by pulling the tissue at the edge to a retracted position followed by pressing clipping or locking the retractor so that the said portion is applied to the skin or said means to anchor the retractor in position holding the tissue retracted.

Preferably, the said portion defines a pad which has an adhering surface defined by a pressure sensitive, sterile adhesive covered by a removable release covering. Specifically, a double-sided adhesive tape may be applied to said pad surface, and the release covering may comprise a release paper or the like so that the adhesive is not exposed until the retractor is to be used.

In an alternative construction, the pad surface may comprise one part of a touch and close fastener, the retractor also including the other part of the touch and close fastener which has on its opposite side a pressure sensitive, sterile adhesive whereby the other part of a touch and close fastener may be applied to the skin to form a means to which the retractor pad may be applied.

The retractor is preferably a disposable moulded plastics component, and there may be an integral hinge connecting the pad to the remainder of the retractor.

In a specific embodiment, the retractor may comprise an elongated, bowed portion at one end of which is the hook means and at the other end of which is the said pad, the bowing of said bowed portion permitting bunching of the retracted flesh without forcing the hook means out of engagement with the flesh and also providing spring resilience to the retractor.

The said bowed portion may be in the form of a curved strip, and the hook means may comprise a portion of the strip turned sharply towards the opposite end of the strip, and at the said end there may be short, spaced, triangular teeth for impaling the tissue.

For holding back the tissue surrounding any particular incisions or aperture, several of the said retractors may be used. The retractors according to the invention have the considerable advantage that hooking the edge of the flesh with the hook means, retracting the flesh and anchoring the retractor can take place in a continuous operation and can be performed swiftly and efficiently amounting simply to a hooking, pulling and a pressing action. In the majority of cases, the retractors will be provided with adhesive surfaces which are applied directly to the skin. The retractors may come in a wide variety of sizes to suit different operations, but they all provide the significant advantage that it is not necessary to have an assistant continuously on hand to hold back the incision or aperture edges whilst the surgeon operates therethrough. Therefore these devices will be useful to general medical practitioners who cannot afford to have medical assistants holding retractors.

The retractors according to the invention furthermore provide considerable advantage over the other type of retractor described herein where the end of the retractor has a sticking plaster applied thereover because the retractor cannot be applied swiftly and in the single continuous motion, but the surgeon must hold the retractor back with one hand whilst he applies the sticking plaster with the other hand. Also, he must pre-prepare the sticking plaster and leave it in a position where it will not become contaminated whilst he makes the incision and applies the retractor and holds same the retracted position. With the retractor of the preferred embodiment of the present invention however he simply hooks, pulls and presses in a continuous operation.

Another advantage of the preferred retractor of the present invention as compared to that using sticking plaster is that it is essentially simple to re-position the retractor if this is required of the surgeon whereas with the prior art arrangement using a sticking plaster, the sticking plaster must be removed and reapplied, and as the sticking plaster takes up space, which could be valuable in the case of an operation through a small incision, re-positioning of the prior art type using sticking plaster if there are already a number of retractors engaging the incision, could be difficult or impossible.

The embodiment of the present invention using an intermediate touch and close fastener as described enhances the repositioning capability, because prior to the making of the incision, the part of the touch an close fastener not applied to the retractor could be pre-applied to the skin, and the retractor can be adjusted in position in relation thereto as long as there is sufficient overlap between the respective parts of the touch and close fasteners to provide an anchorage.

Upon completion of the surgeon's work or examination through the incision or aperture, the retractors are simply removed and the incision repaired.

There is furthermore considerable advantage in providing the retractor with the bowed portion mentioned if that bowed portion is of sufficient resiliency to cause an inherent tension in the retractor when it is applied. The bowed portion operates in this manner. When the hooked end is engaged in the tissue and the retractor pulled, the bowed portion tends to flatten somewhat under the tension pulling forces, and after the adhering surface is applied anchoring the retractor, the bowed portion remains in this more flattened out condition, but constantly by virtue of its resilience it tries to return to the bowed position, which creates the internal tension applied to the tissue which limits the tendency of the hooked end to spring out during the surgeon's work.

The springiness furthermore in the bowed portion also ensures that there will be no unnecessary damage to the tissue as a result of the application of the retractor.

The bowed portion provides a significant improvement as explained herein, and in addition therefore the invention provides in a second aspect a rectractor for hand application and comprising at one end hook means for hooking onto the edge of an aperture or incision in tissue whereby with the hook means engaging the flesh, the edge of the aperture or incision can be pulled back by pulling the retractor to improve access through said aperture or incision, and the retractor at a location spaced from said hook means can be anchored to keep the tissue in the held back position, wherein the said hook means is provided at one end of a bowed portion, which bowing permits bunching of the pulled back tissue without forcing the hook means out of engagement with the flesh.

Any adhesive selected for the retractor, and which is to be applied directly to the skin will require to be such as to give good adhesion to the skin without causing any invasion of the skin over the period, typically several hours, during which the retractor will be applied to the skin, but there are several suitable adhesives sold as double-sided tape, for this purpose, and such adhesives include the following.

Acrylic based hypo allergenic adhesives such as that used in the radiation tolerant, 3mm polyethylene double coated medical tape sold by the 3M company under number 1509.

Instead of using a touch and close fastener arrangement, two members which interlock can be used, one of which is applied to the skin at the aperture or incision and the other of which is formed as part of the retractor. Also, the retractor end may be provided with spring clip means used as spring jaws adapted to clip resiliently onto the tissue for anchoring the retractor. Such jaws may be formed integrally with the retractor.

An embodiment of the invention will now be described, by way of example, with reference to the accompanying drawings, wherein:

FIG. 1A is a perspective concept view of an embodiment of the invention;

FIG. 1B shows a perspective view of a specific design of retractor based upon the embodiment of the invention shown in FIG. 1A;

FIG. 2 is a perspective underneath view of the portion of the retractor of FIG. 1B showing removal of the release covering paper;

FIG. 3 is a plan view showing two retractors as shown in FIG. 1B in use;

FIG. 4 is a sectional elevation of the arrangement as shown in FIG. 3, the section being taken on the line IV—IV in FIG. 3;

Figure 7:
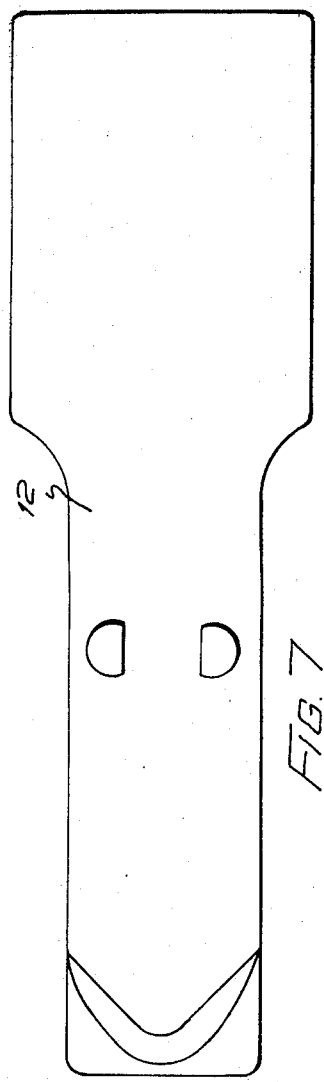
Figure 8:
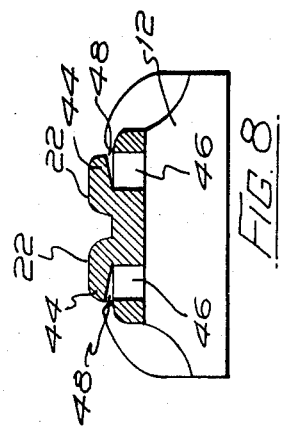
Figure 9:
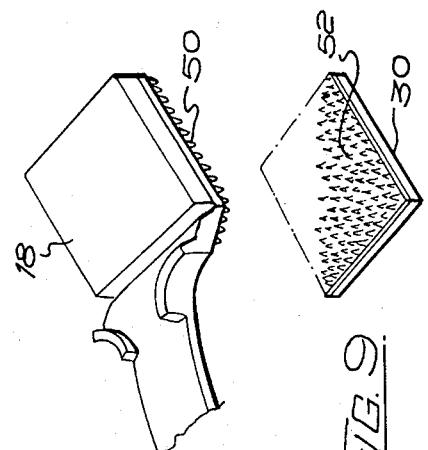

FIGS. 5, 6 and 7 respectively show a plan, a part-sectional elevation, and an underneath plan of the retractor shown in FIG. 1;

FIG. 8 is a sectional elevation taken on the line VIII—VIII in FIG. 6;

FIG. 9 is a perspective elevation of a portion of a modified retractor; and

Figure 10:
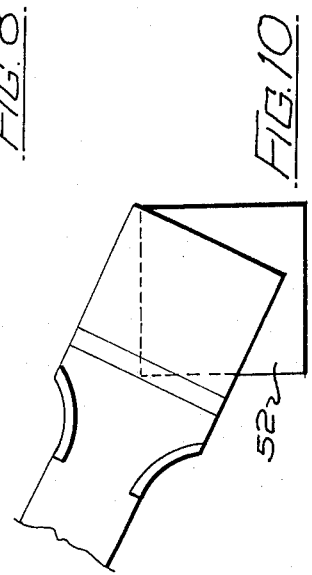

FIG. 10 is a plan view of the arrangement of FIG. 9 showing its utilisation.

In FIG. 1A there is shown a tissue retractor which is preferably in disposable plastics material and of suitable sterility to be used in connection with tissue incisions. The retractor may be suitably moulded or otherwise formed, and it comprises a flat pad portion a to one edge of which is connected a convex arm portion b, and at the free end of the arm portion b is a hook end c having a pair of teeth d.

To the underside of the flat portion a is applied an adhesive e covered by a release paper or the like f. The adhesive e may be a double sided adhesive tape.

To use the device as shown in FIG. 1A, in conjunction with a similar device, an incision is made in the skin, and the opposite edges of the skin are held back by two devices each as shown in FIG. 1A. To use the devices, the release paper f is first of all removed, and then after the incision is made, the hook ends c of the devices are engaged in the incision sides with the teeth d engaging the tissue, and then the retractors are pulled apart until the incision is open to the required degree, and then the flat portions a are simply pressed to the marginal regions of the skin surface and become adhered thereto by virtue of the adhesive e. Adhesive e will be suitably selected so as not to cause invasion of the skin during the period when the operation through the incision will be conducted.

Upon completion of the operation, the retractors are simply removed.

The material of the retractor is preferably X-ray detectible so that if a portion breaks off it can readily be located if it is inside the patients' body.

Referring to the remaining drawings, in FIG. 1B is shown a specific design of retractor 10 according to the invention. The retractor is a one-piece rigid plastics component, preferably made of polypropylene and will be of a sterile nature as it is for utilisation in medical operations, as will be explained. The retractor comprises essentially a bowed portion 12 which is bowed upwardly, and has at one end a sharply turned back portion 14 defining a hook means, and portion 14 defines two sharp tangs 16 which are of triangular form and which are for impaling the tissue which is to be retracted by the retractor. The bowed portion 12 leads to a pad 18 at the opposite end, the pad 18 on the surface 20 thereof being provided with a pressure sensitive adhesive which, as will be explained is applied to the skin to anchor the retractor. The adhesive will be of a sterile nature so as not to invade the skin to which it is applied, and it may be in the form of double sided adhesive tape with a release covering applied thereto to protect the adhesive until the retractor is to be used. At the crest of the bowed portion 12 there are formed therein two stud portions 22 which are for the reception and trapping of a suture strand which the surgeon may use in an operation. The details of the studs 22 will be given hereinafter.

Towards the end of the bowed portion 12 where it meets the pad 18 are finger gripping edges 24 to enable the holding and manipulation of the retractor in the application of same as will be explained herein.

A flexible integral hinge 26 connects the bowed portion 12 and the pad 18 which facilitates the manufacture of the retractor, which manufacture will indeed be by injection moulding.

Use of the retractor is simple in that, as shown in FIG. 2 when the retractor is to be used the release paper 28 covering the adhesive surface 30 is removed. The release paper may be larger than the adhesive surface and may overlap the pad 20 so that the overlap provides a thumb grip enabling the paper to be gripped and peeled away easily. In the next stage, referring to FIG. 3, after say an incision 32 is made in the animal or human body in relation to which an operation is to be carried out, the hooked end 14 of the retractor is placed in the incision 32 and the teeth 16 are impaled in the tissue defining the hole of the incision as shown at 34, and the retractor is then pulled in the direction of arrow 36 in FIG. 3 pulling the flesh to the retracted position 38. This is facilitated by virtue of the bowing of portion 12 and proceeding the portions 24. It is to be noticed as shown in FIG. 4 that the flesh in the area of the retracted edge 34 piles up in bunches as shown at 40, and the bowing of the portion 12 provides the advantage of accommodating this bunch without giving rise to the forces from the flesh in the region 40 which might tend to wedge the teeth 16 out of the flesh edge 34. Fig. 3 shows that two retractors are used to retract opposite sides of the incision 32 in order to open up the incision to enable the surgeon to have a working aperture, and the dotted lines also indicate that as many retractors as are required can be used for the opening of the incision to the required extent. The surgeon or assistant applying the retractor holds same by the ledges 24 with the forefinger and thumbas the tissue is pulled back, and this has the effect of somewhat flattening or straightening out the bowing of portion 12 from the more convex shape shown in dotted lines by reference 42 in FIG. 4. When the tissue has been retracted to a sufficient extent, the person applying the retractor by manipulation of the hand simply presses the pad 18 down firmly onto the skin with the top of the middle finger whilst still gripping ledges 24 so that the adhesive 30 will be applied thereto, and will form an anchorage point for the retractor, keeping the flesh retracted as shown in FIGS. 3 and 4. When the retractor is in this condition, the bowed portion 12 will in fact be strained by the tension in the retractor, and will tend to return to the dotted line position shown at 42 in FIG. 4, which has the effect of keeping a tensile force on the tissue in the region of the edge 34 of the portion 40 ensuring a firm and secure holding of the tissue.

FIGS. 5, 6 and 7 show the retractor of FIG. 1B in more detail and are to scale.

FIG. 8 is useful in illustrating the form of the studs 22, and shows that these studs are formed out of the body of the material of section 12. The studs have cap portions 44 which overlie apertures 46 through portion 12, but which are in the form of wings defining slots 48 into which sutures for example which may be anchored in the working area of the operation may be slipped to hold same in position so that they do not interfere with the operation.

FIGS. 9 and 10 show a modification in which, instead of providing the adhesive surface 30 on the underside of pad 18 as shown in FIG. 4, the underside of pad 18 is provided with one part 50 of the touch and close fastener arrangement, whilst the other part 52 has on its rear side thereof a pressure sensitive adhesive which is the same as the pressure sensitive adhesive 30 in the FIG. 1B embodiment. In the utilisation of this embodiment, the surgeon or assistant pre-positions the part 52 of the touch and close fastener using the adhesive surface 30, and in the subsequent application of the retractor, the surface 50 is simply applied and locked to the surface 52 to hold the retractor in position. FIG. 10 shows that this arrangement has the advantage that the surface 50 need not exactly overlap the surface 52 to provide the adhesion and anchoring, and therefore if the retractor needs to be adjusted, the part 50 is detached from the part 52, the retractor is adjusted and then the parts 50 and 52 are once more brought together. This means that there is no need to disconnect the adhesive surface from the skin, which may be a disadvantage if the adhesive is not capable of connection and disconnection to the skin repeatedly. If the adhesive can be disconnected and re-applied to the skin without losing any adhesion, then the modification of FIGS. 9 and 10 is not necessary, and the retractor of FIGS. 1 to 8 can be re-positioned readily.

In a further modification, there is a retractor part, such as part 52, which is struck to the skin, but instead of the upper surface having a touch and close fastener component, it may have another complementary coupling means adapted to couple with complementary coupling means on the body portion of the retractor. Thus the end of the body portion of the retractor may simply hook over part stuck to the skin to be retained thereby by virtue of the tension in the retractor. In yet a further modification, the retractor may be provided with a pair of formations which can be sprung apart so that a portion of tissue can be placed between said formations so that it can be clipped thereby when the formations are released, thereby to provide the anchorage of the retractor to the skin.

When the retractors are one piece units, and as illustrated in FIG. 1A, they may conveniently be moulded, for example injection moulded, in groups such as groups of four, then the adhesive is applied as a strip across the pads 18, and the groups can then be packaged so as to be broken off easily by the surgeon when he requires to use one. The retractor will therefore be readily useable and highly functional as a surgeon working alone who is in need of a retractor must have a means which he can handle and apply quickly and easily, and the retractor of the invention provides such a means in that the device can be applied simply by removing the release paper then manipulating the hand in a continuous movement to hook pull and apply the device by pressure application. The bowing of the front end of the retractor ensures the effective holding and tensioning of the retractor.

It is to be appreciated that the retractor will require to be sterile in being used in surgical operations, and that any adhesive which is used for sticking direct to the skin must be of a nature not to invade the skin. It is recognised however that the retractor can be used in a fashion which involves applying a locking portion of the retractor directly to a means previously applied to or over the skin which can form an anchoring point, and in this case if an adhesive is used and does not touch the skin, then it may not require to be sterile.

Other constructions are possible within the scope of the present invention. Thus, the hooking end of the retractor need not be claw shaped, but could simply be provided with a bent portion or a ridge or any other means which will provide a grip or hold on the edge of the incision or aperture. Although it is preferred that the retractor should be made in plastics material and should be disposable, it is also possible to provide retractors according to the invention in metal which can be re-used after appropriate sterilisation.

The retractor according to the invention, appropriately sized, is useable in virtually any application involving an incision, but a number of specific applications where the retractor can be used with considerable advantage are as follows:

Accident and emergency work where the operator is often single handed.

Small orifice procedures for biopsy of glands and organs.

Emergency procedures, intra-venous cut-down, tracheotomy.

Renal dialysis, where personnel involved in surgical procedures need to be at a minimum.

It finds a particular use in small delicate procedures where accurate fixation of the operating field would hitherto have been provided by sutures, e.g. microsurgery, opthalmic surgery, hypospadius repair, blepharoplasty and nerve and tendon repair.

I claim:

1. A retractor for hand application and comprising (a) a rigid body portion adapted to be gripped by the fingers of one hand, (b) a head portion at one end of the body portion and comprising hook means for engaging the edge of an aperture or incision in tissue;
   (c) a tail portion at the other end of the body portion; and
   (d) pressure sensitive adhering surface on an underside surface of the tail portion,
whereby said rigid body portion can be gripped by the fingers of one hand, the hook means engaged in an aperture or incision, the retractor pulled to open the aperture or incision and the tail portion fixed to a patient by the simple step of pressing the pressure sensitive adhering surface against the skin or other surface complementary to said pressure sensitive adhering surface to thereby anchor the retractor and maintain the edge of the aperture or incision in a retracted position.

2. A retractor according to claim 1 wherein the adhering surface of the tail portion comprises a pressure sensitive sterile adhesive covered by a removable release covering.

3. A retractor according to claim 1 wherein the tail portion comprises a two part touch and close fastener, one part of which is provided with a pressure sensitive sterile adhesive that is adapted to be applied against the skin.

4. A retractor according to claim 1 wherein the retractor rigid body portion comprises a moulded plastics component.

5. A retractor according to claim 1 wherein the said tail portion is connected to the body portion of the retractor by means of an integral hinge.

6. A retractor according to claim 1 wherein the rigid body portion comprises an elongated, bowed portion at one end of which is the hook means and at the other end of which is the said tail portion, the deformation of said bowed portion causing bunching of the retracted tissue without permitting the hook means to come out of engagement with the tissue and also providing spring resistance to the retractor.

7. A retractor according to claim 6 wherein said bowed portion is in the form of a curved strip and the hook means is a section of the strip turned sharply towards the opposite end of the strip, and the end of said section has short, spaced triangular teeth for impaling the flesh.

8. A retractor for hand application and comprising
   (a) a rigid body portion adapted to be gripped by the fingers of one hand,
   (b) a head portion at one end of the body portion and comprising hook means for engaging the edge of an aperture or incision in tissue,
   (c) a tail portion at the other end of the body portion,
   (d) means on the tail portion enabling the retractor to be anchored to the skin,
   (e) the said rigid body portion being bowed from the head portion to the tail portion thus enabling the tissue engaged by the hook portion to bunch when retracted while limiting the tendency of the bunched tissue to disengage the hook portion.

9. A retractor according to claim 8 wherein said bowed portion is in the form of a curved strip and the hook means is a section of the strip turned sharply towards the opposite end of the strip, and the end of the section has short, spaced triangular teeth for impaling the tissue.

10. A retractor according to claim 9 wherein the retractor comprises a moulded plastics component.

11. A retractor according to claim 1 wherein the body portion is provided with projections intermediate the ends of the body portion to which medical sutures may be tied.

12. A retractor according to claim 8 wherein the body portion is provided with projections intermediate the ends of the body portion to which medical sutures may be tied.

* * * * *